United States Patent [19]
Talley et al.

[11] Patent Number: 5,696,143
[45] Date of Patent: Dec. 9, 1997

[54] BENZ [G] INDAZOLYL DERIVATIVES FOR THE TREATMENT OF INFLAMMATION

[76] Inventors: John J. Talley, 8772 Pine Ave.; Stephen R. Bertenshaw, 8758 Pine Ave., both of Brentwood, Mo. 63114; Roland S. Rogers, 7431 Arlington Dr., Richmond Heights, Mo. 63117

[21] Appl. No.: 309,294

[22] Filed: Sep. 20, 1994

[51] Int. Cl.$^6$ .................. A61K 31/415; C07D 231/54
[52] U.S. Cl. .................. 514/403; 548/359.1
[58] Field of Search .................. 548/359.1; 514/403

[56] References Cited

U.S. PATENT DOCUMENTS

| | | |
|---|---|---|
| 3,404,157 | 10/1968 | McEvoy et al. . |
| 3,940,418 | 2/1976 | Hamilton . |
| 5,134,155 | 7/1992 | Connolly et al. . |
| 5,315,012 | 5/1994 | Connolly et al. . |
| 5,508,426 | 4/1996 | Talley et al. .................. 548/359.1 |

FOREIGN PATENT DOCUMENTS

94/15932   7/1994   WIPO .

OTHER PUBLICATIONS

E. Becalli, et al, *Chemical Abstracts*, 113, 40087 (1990).
M.M. Hashem et al, *J. Med. Chem.*, 19, 229 (1976).
Robert W. Hamilton, *J. Heterocyclic Chem.*, 13, 545 (1976).

*Primary Examiner*—Robert W. Ramsuer

[57] ABSTRACT

A class of benz[g]indazolyl derivatives is described for use in treating inflammation and inflammation-related disorders. Compounds of particular interest are defined by Formula I

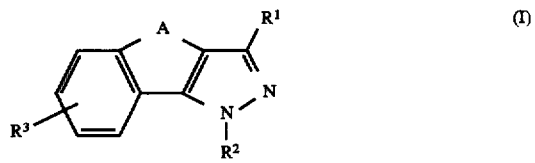

wherein A is —CH=CH—; wherein $R^1$ is selected from lower haloalkyl, cyano, lower alkoxycarbonyl, lower N-alkylaminocarbonyl, N-phenylaminocarbonyl, lower N,N-dialkylaminocarbonyl and lower N-alkyl-N-phenylaminocarbonyl; wherein $R^2$ is phenyl substituted at a substitutable position with a radical selected from lower alkylsulfonyl and sulfamyl; and wherein $R^3$ is one or more radicals selected from halo, lower alkylthio, lower alkylsulfinyl, lower alkyl, cyano, lower alkoxycarbonyl, aminocarbonyl, lower N-alkylaminocarbonyl, lower haloalkyl, hydroxyl, lower alkoxy, lower hydroxyalkyl, lower haloalkoxy, amino, lower N,N-dialkylamino and nitro; or a pharmaceutically-acceptable salt thereof.

32 Claims, No Drawings

BENZ [G] INDAZOLYL DERIVATIVES FOR THE TREATMENT OF INFLAMMATION

FIELD OF THE INVENTION

This invention is in the field of antiinflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase II (COX II)" or "prostaglandin GH synthase II") provides a viable target of inhibition which more effectively reduces inflammation and produces fewer and less drastic side effects.

The novel compounds described herein are such safe and also effective antiinflammatory agents. The invention compounds are found to show usefulness in vivo as antiinflammatory agents with minimal side effects. The compounds described herein preferably selectively inhibit cyclooxygenase II over cyclooxygenase I.

Substituted pyrazoles having antiinflammatory activity are described in copending applications Ser. No. 08/160,594 now U.S. Pat. No. 5,466,823 and Ser. No. 08/160,553 now U.S. Pat. No. 5,475,018.

Fused tricyclic pyrazoles having a saturated ring bridging the pyrazole and a phenyl radical have been previously described as HMG-CoA reductase inhibitors in U.S. Pat. Nos. 5,134,155 and 5,315,012, and as antibiotics by M. Hashem et al [*J. Med. Chem.*, 19, 229 (1976)].

U.S. Pat. No. 3,940,418 and *J. Heterocyclic Chem.*, 13, 545 (1976) describe tricyclic benz[g]indazoles and 4,5-dihydrobenz[g]indazoles as antiinflammatory agents. Specifically, [7-chloro-1-phenyl-1H-benz[g]indazol-3-yl] carboxylic acid and methyl (7-chloro-1-phenyl-1H-benz[g] indazol-3-yl)carboxylate are described.

However, the unsaturated benz[g]indazolyl derivatives of the present invention have not been previously described.

DESCRIPTION OF THE INVENTION

A class of compounds useful in treating inflammation-related disorders is defined by Formula I:

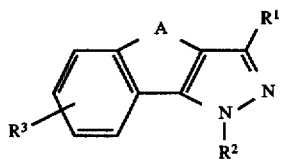

wherein A is $-(CH_2)_m-CH=CH-(CH_2)_n-$;

wherein m is 0 or 1;

wherein n is 0 or 1;

wherein $R^1$ is selected from hydrido, halo, haloalkyl, cyano, nitro, formyl, alkoxycarbonyl, carboxyl, carboxyalkyl, alkoxycarbonylalkyl, amidino, cyanoamidino, aminocarbonyl, alkoxy, alkoxyalkyl, aminocarbonylalkyl, N-monoalkylaminocarbonyl, N-arylaminocarbonyl, N,N-dialkylaminocarbonyl, N-alkyl-N-arylaminocarbonyl, alkylcarbonyl, alkylcarbonylalkyl, hydroxyalkyl, alkylthio, alkylsulfinyl, alkylsulfonyl, alkylthioalkyl, alkylsulfinylalkyl, alkylsulfonylalkyl, N-alkylsulfamyl, N-arylsulfamyl, arylsulfonyl, N,N-dialkylsulfamyl, N-alkyl-N-arylsulfamyl and heterocyclic;

wherein $R^2$ is selected from aryl and heteroaryl, wherein $R^2$ is optionally substituted at a substitutable position with one or more radicals selected from alkylsulfonyl, sulfamyl, halo, alkyl, alkoxy, hydroxyl and haloalkyl; and wherein $R^3$ is one or more radicals selected from hydrido, halo, alkylthio, alkylsulfinyl, alkyl, alkylsulfonyl, cyano, carboxyl, alkoxycarbonyl, aminocarbonyl, N-monoalkylaminocarbonyl, N-arylaminocarbonyl, N,N-dialkylaminocarbonyl, N-alkyl-N-arylaminocarbonyl, haloalkyl, hydroxyl, alkoxy, hydroxyalkyl, haloalkoxy, sulfamyl, N-alkylsulfamyl, amino, N-alkylamino, N,N-dialkylamino, heterocyclic, nitro and acylamino;

provided $R^2$ is substituted when $R^3$ is halo;

or a pharmaceutically-acceptable salt thereof.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of Formula I would be useful to treat arthritis, including but not limited to rheumatoid arthritis, spondyloarthopathies, gouty arthritis, osteoarthritis, systemic lupus erythematosus and juvenile arthritis. Such compounds of Formula I would be useful in the treatment of asthma, bronchitis, menstrual cramps, tendinitis, bursitis, and skin related conditions such as psoriasis, eczema, burns and dermatitis. Compounds of Formula I also would be useful to treat gastrointestinal conditions such as inflammatory bowel disease, Crohn's disease, gastritis, irritable bowel syndrome and ulcerative colitis and for the prevention of colorectal cancer. Compounds of Formula I would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds are useful as antiinflammatory agents, such as for the treatment of arthritis, with the additional benefit of having significantly less harmful side effects.

The present invention preferably includes compounds which selectively inhibit cyclooxygenase II over cyclooxygenase I. Preferably, the compounds have a cyclooxygenase II $IC_{50}$ of less than about 0.2 µM, and also have a selectivity ratio of cyclooxygenase II inhibition over cyclooxygenase I inhibition of at least 50, and more preferably of at least 100. Even more preferably, the compounds have a cyclooxygenase I $IC_{50}$ of greater than about 1 µM, and more preferably of greater than 10 µM. Such preferred selectivity may indicate an ability to reduce the incidence of common NSAID-induced side effects.

A preferred class of compounds consists of those compounds of Formula I wherein A is —$(CH_2)_m$—CH=CH—$(CH_2)_n$—;

wherein m is 0 or 1;

wherein n is 0 or 1;

wherein $R^1$ is selected from halo, lower haloalkyl, cyano, nitro, formyl, lower alkoxycarbonyl, lower carboxyalkyl, lower alkoxycarbonylalkyl, amidino, cyanoamidino, lower alkoxy, lower alkoxyalkyl, lower aminocarbonylalkyl, lower N-monoalkylaminocarbonyl, N-phenylaminocarbonyl, lower N,N-dialkylaminocarbonyl, lower N-alkyl-N-phenylaminocarbonyl, lower alkylcarbonyl, lower alkylcarbonylalkyl, lower hydroxyalkyl, lower alkylthio, lower alkylsulfinyl, lower alkylsulfonyl, lower alkylthioalkyl, lower alkylsulfinylalkyl, lower alkylsulfonylalkyl, lower N-alkylsulfamyl, N-phenylsulfamyl, phenylsulfonyl, lower N,N-dialkylsulfamyl, lower N-alkyl-N-phenylsulfamyl and five-seven membered heterocyclic;

wherein $R^2$ is selected from phenyl and five or six membered heteroaryl, wherein $R^2$ is optionally substituted at a substitutable position with one or more radicals selected from lower alkylsulfonyl, sulfamyl, halo, lower alkyl, lower alkoxy, hydroxyl and lower haloalkyl; and wherein $R^3$ is one or more radicals selected from halo, lower alkylthio, lower alkylsulfinyl, lower alkyl, lower alkylsulfonyl, cyano, carboxyl, lower alkoxycarbonyl, aminocarbonyl, lower N-monoalkylaminocarbonyl, N-phenylaminocarbonyl, lower N,N-dialkylaminocarbonyl, lower N-alkyl-N-phenylaminocarbonyl, lower haloalkyl, hydroxyl, lower alkoxy, lower hydroxyalkyl, lower haloalkoxy, sulfamyl, lower N-alkylsulfamyl, amino, lower N-alkylamino, lower N,N-dialkylamino, five-seven membered heterocyclic, nitro and acylamino;

or a pharmaceutically-acceptable salt thereof.

A more preferred class of compounds consists of those compounds of Formula I wherein A is CH=CH—; wherein $R^1$ is selected from halo, lower haloalkyl, cyano, nitro, formyl, lower alkoxycarbonyl, lower carboxyalkyl, lower alkoxy, lower N-monoalkylaminocarbonyl, N-phenylaminocarbonyl, lower N,N-dialkylaminocarbonyl, lower N-alkyl-N-phenylaminocarbonyl, lower alkylcarbonyl and lower hydroxyalkyl; wherein $R^2$ is phenyl substituted at a substitutable position with a radical selected from lower alkylsulfonyl and sulfamyl; and wherein $R^3$ is one or more radicals selected from halo, lower alkylthio, lower alkylsulfinyl, lower alkyl, lower alkylsulfonyl, cyano, lower carboxyl, lower alkoxycarbonyl, aminocarbonyl, lower N-monoalkylaminocarbonyl, N-phenylaminocarbonyl, lower N,N-dialkylaminocarbonyl, lower N-alkyl-N-phenylaminocarbonyl, lower haloalkyl, hydroxyl, lower alkoxy, lower hydroxyalkyl, lower haloalkoxy, amino, lower N-alkylamino, lower N,N-dialkylamino, nitro and acylamino; or a pharmaceutically-acceptable salt thereof.

An even more preferred class of compounds consists of those compounds of Formula I wherein A is —CH=CH—; wherein $R^1$ is selected from lower haloalkyl, cyano, lower alkoxycarbonyl, lower N-monoalkylaminocarbonyl, N-phenylaminocarbonyl, lower N,N-dialkylaminocarbonyl and lower N-alkyl-N-phenylaminocarbonyl; wherein $R^2$ is phenyl substituted at a substitutable position with a radical selected from lower alkylsulfonyl and sulfamyl; and wherein $R^3$ is one or more radicals selected from halo, lower alkylthio, lower alkylsulfinyl, lower alkyl, cyano, lower alkoxycarbonyl, aminocarbonyl, lower N-monoalkylaminocarbonyl, lower haloalkyl, hydroxyl, lower alkoxy, lower hydroxyalkyl, lower haloalkoxy, amino, lower N,N-dialkylamino and nitro; or a pharmaceutically-acceptable salt thereof.

A class of compounds of particular interest consists of those compounds of Formula I wherein A is —CH=CH—; wherein $R^1$ is selected from fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, N-methylaminocarbonyl, N-phenylaminocarbonyl, N,N-dimethylaminocarbonyl and N-methyl-N-phenylaminocarbonyl; wherein $R^2$ is phenyl substituted at a substitutable position with methylsulfonyl or sulfamyl; and wherein $R^3$ is one or more radicals selected from fluoro, chloro, bromo, methylthio, ethylthio, isopropylthio, tert-butylthio, isobutylthio, hexylthio, methylsulfinyl, ethylsulfinyl, isopropylsulfinyl, tert-butylsulfinyl, isobutylsulfinyl, hexylsulfinyl, methyl, ethyl, isopropyl, tert-butyl, isobutyl, hexyl, cyano, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, aminocarbonyl, N-methylaminocarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, hydroxymethyl, trifluoromethoxy, amino, N,N-dimethylamino and nitro; or a pharmaceutically-acceptable salt thereof.

A family of specific compounds of particular interest within Formula I consists of compounds and pharmaceutically-acceptable salts thereof as follows:

4-[6-chloro-7-methoxy-1H-benz[g]indazol-1-yl]benzenesulfonamide;

[1-(4-aminosulfonylphenyl)-6-chloro-7-methoxy-1H-benz[g]indazol-3-yl]carbonitrile;

methyl [1-(4-aminosulfonylphenyl)-6-chloro-7-methoxy-1H-benz[g]indazol-3-yl]carboxylate;

ethyl [1-(4-aminosulfonylphenyl)-6-chloro-7-methoxy-1H-benz[g]indazol-3-yl]carboxylate;

N-methyl [1-(4-aminosulfonylphenyl)-6-chloro-7-methoxy-1H-benz[g]indazol-3-yl]carboxamide;

6-chloro-7-methoxy-1-(4-methylsulfonylphenyl)-1H-benz[g]indazole;

[1-(4-methylsulfonylphenyl)-6-chloro-7-methoxy-1H-benz[g]indazol-3-yl]carbonitrile;

methyl [1-(4-methylsulfonylphenyl)-6-chloro-7-methoxy-1H-benz[g]indazol-3-yl]carboxylate;

ethyl [1-(4-methylsulfonylphenyl)-6-chloro-7-methoxy-1H-benz[g]indazol-3-yl]carboxylate;

N-methyl [1-(4-methylsulfonylphenyl)-6-chloro-7-methoxy-1H-benz[g]indazol-3-yl]carboxamide;

[1-(4-methylsulfonylphenyl)-3-(difluoromethyl)-1H-benz[g]indazol-7-yl]carboxylic acid;

methyl [1-(4-methylsulfonylphenyl)-3-(difluoromethyl)-1H-benz[g]indazol-7-yl]carboxylate;

[1-(4-methylsulfonylphenyl)-3-(difluoromethyl)-1H-benz[g]indazol-7-yl]carbonitrile;

3-(difluoromethyl)-7-hydroxy-1-(4-methylsulfonylphenyl)-1H-benz[g]indazole;

3-(difluoromethyl)-7-hydroxymethyl-1-(4-methylsulfonylphenyl)-1H-benz[g]indazole;

3-(difluoromethyl)-1-(4-methylsulfonylphenyl)-7-trifluoromethoxy-1H-benz[g]indazole;

7-chloro-3-(difluoromethyl)-1-(4-methylsulfonylphenyl)-1H-benz[g]indazole;

3-(difluoromethyl)-7-fluoro-1-(4-methylsulfonylphenyl)-1H-benz[g]indazole;

7-bromo-3-(difluoromethyl)-1-(4-methylsulfonylphenyl)-1H-benz[g]indazole;

3-(difluoromethyl)-7-methyl-1-(4-methylsulfonylphenyl)-1H-benz[g]indazole;

3-(difluoromethyl)-7-methoxy-1-(4-methylsulfonylphenyl)-1H-benz[g]indazole;

3-(difluoromethyl)-6,7-methylenedioxy-1-(4-methylsulfonylphenyl)-1H-benz[g]indazole;

3-(difluoromethyl)-7-dimethylamino-1-(4-methylsulfonylphenyl)-1H-benz[g]indazole;

3-(difluoromethyl)-6-fluoro-7-methoxy-1-(4-methylsulfonylphenyl)-1H-benz[g]indazole;

6-chloro-3-(difluoromethyl)-7-fluoro-1-(4-methylsulfonylphenyl)-1H-benz[g]indazole;

6-chloro-3-(difluoromethyl)-7-methyl-1-(4-methylsulfonylphenyl)-1H-benz[g]indazole;

3-(difluoromethyl)-6-fluoro-7-methyl-1-(4-methylsulfonylphenyl)-1H-benz[g]indazole;

6,7-dichloro-3-(difluoromethyl)-1-(4-methylsulfonylphenyl)-1H-benz[g]indazole;

6,7-difluoro-3-(difluoromethyl)-1-(4-methylsulfonylphenyl)-1H-benz[g]indazole;

3-(difluoromethyl)-1-(4-methylsulfonylphenyl)-7-methylthio-1H-benz[g]indazole;

6-chloro-3-(difluoromethyl)-1-(4-methylsulfonylphenyl)-7-methylthio-1H-benz[g]indazole;

3-(difluoromethyl)-1-(4-methylsulfonylphenyl)-7-methylsulfinyl-1H-benz[g]indazole;

6-chloro-3-(difluoromethyl)-7-methylsulfinyl-1-(4-methylsulfonylphenyl)-1H-benz[g]indazole;

[1-(4-methylsulfonylphenyl)-3-(trifluoromethyl)-1H-benz[g]indazol-7-yl]carboxylic acid;

methyl [1-(4-methylsulfonylphenyl)-3-(trifluoromethyl)-1H-benz[g]indazol-7-yl]carboxylate;

[1-(4-methylsulfonylphenyl)-3-(trifluoromethyl)-1H-benz[g]indazol-7-yl]carbonitrile;

7-hydroxy-1-(4-methylsulfonylphenyl)-3-(trifluoromethyl)-1H-benz[g]indazole;

7-hydroxymethyl-1-(4-methylsulfonylphenyl)-3-(trifluoromethyl)-1H-benz[g]indazole;

1-(4-methylsulfonylphenyl)-7-trifluoromethoxy-3-(trifluoromethyl)-1H-benz[g]indazole;

7-chloro-1-(4-methylsulfonylphenyl)-3-(trifluoromethyl)-1H-benz[g]indazole;

7-fluoro-1-(4-methylsulfonylphenyl)-3-(trifluoromethyl)-1H-benz[g]indazole;

7-bromo-1-(4-methylsulfonylphenyl)-3-(trifluoromethyl)-1H-benz[g]indazole;

7-methyl-1-(4-methylsulfonylphenyl)-3-(trifluoromethyl)-1H-benz[g]indazole;

7-methoxy-1-(4-methylsulfonylphenyl)-3-(trifluoromethyl)-1H-benz[g]indazole;

6,7-methylenedioxy-1-(4-methylsulfonylphenyl)-3-(trifluoromethyl)-1H-benz[g]indazole;

7-dimethylamino-1-(4-methylsulfonylphenyl)-3-(trifluoromethyl)-1H-benz[g]indazole;

6-fluoro-7-methoxy-1-(4-methylsulfonylphenyl)-3-(trifluoromethyl)-1H-benz[g]indazole;

6-chloro-7-fluoro-1-(4-methylsulfonylphenyl)-3-(trifluoromethyl)-1H-benz[g]indazole;

6-chloro-7-methyl-1-(4-methylsulfonylphenyl)-3-(trifluoromethyl)-1H-benz[g]indazole;

6-fluoro-7-methyl-1-(4-methylsulfonylphenyl)-3-(trifluoromethyl)-1H-benz[g]indazole;

6,7-dichloro-1-(4-methylsulfonylphenyl)-3-(trifluoromethyl)-1H-benz[g]indazole;

6,7-difluoro-1-(4-methylsulfonylphenyl)-3-(trifluoromethyl)-1H-benz[g]indazole;

1-(4-methylsulfonylphenyl)-7-methylthio-3-(trifluoromethyl)-1H-benz[g]indazole;

6-chloro-1-(4-methylsulfonylphenyl)-7-methylthio-3-(trifluoromethyl)-1H-benz[g]indazole;

7-methylsulfinyl-1-(4-methylsulfonylphenyl)-3-(trifluoromethyl)-1H-benz[g]indazole;

6-chloro-7-methylsulfinyl-1-(4-methylsulfonylphenyl)-3-(trifluoromethyl)-1H-benz[g]indazole;

6-chloro-7-methoxy-1-(4-methylsulfonylphenyl)-3-(trifluoromethyl)-1H-benz[g]indazole;

[1-(4-aminosulfonylphenyl)-3-(difluoromethyl)-1H-benz[g]indazol-7-yl]carboxylic acid;

methyl [1-(4-aminosulfonylphenyl)-3-(difluoromethyl)-1H-benz[g]indazol-7-yl]carboxylate;

[1-(4-aminosulfonylphenyl)-3-(difluoromethyl)-1H-benz[g]indazol-7-yl]carbonitrile;

4-[3-(difluoromethyl)-7-hydroxy-1H-benz[g]indazol-1-yl]benzenesulfonamide;

4-[3-(difluoromethyl)-7-hydroxymethyl-1H-benz[g]indazol-1-yl]benzenesulfonamide;

4-[3-(difluoromethyl)-7-trifluoromethoxy-1H-benz[g]indazol-1-yl]benzenesulfonamide;

4-[7-chloro-3-(difluoromethyl)-1H-benz[g]indazol-1-yl]benzenesulfonamide;

4-[3-(difluoromethyl)-7-fluoro-1H-benz[g]indazol-1-yl]benzenesulfonamide;

4-[7-bromo-3-(difluoromethyl)-1H-benz[g]indazol-1-yl]benzenesulfonamide;

4-[3-(difluoromethyl)-7-methyl-1H-benz[g]indazol-1-yl]benzenesulfonamide;

4-[3-(difluoromethyl)-7-methoxy-1H-benz[g]indazol-1-yl]benzenesulfonamide;

4-[3-(difluoromethyl)-6,7-methylenedioxy-1H-benz[g]indazol-1-yl]benzenesulfonamide;

4-[3-(difluoromethyl)-7-dimethylamino-1H-benz[g]indazol-1-yl]benzenesulfonamide;

4-[3-(difluoromethyl)-6-fluoro-7-methoxy-1H-benz[g]indazol-1-yl]benzenesulfonamide;

4-[6-chloro-3-(difluoromethyl)-7-fluoro-1H-benz[g]indazol-1-yl]benzenesulfonamide;

4-[6-chloro-3-(difluoromethyl)-7-methyl-1H-benz[g]indazol-1-yl]benzenesulfonamide;

4-[3-(difluoromethyl)-6-fluoro-7-methyl-1H-benz[g]indazol-1-yl]benzenesulfonamide;

4-[6,7-dichloro-3-(difluoromethyl)-1H-benz[g]indazol-1-yl]benzenesulfonamide;

4-[6,7-difluoro-3-(difluoromethyl)-1H-benz[g]indazol-1-yl]benzenesulfonamide;

4-[3-(difluoromethyl)-7-methylthio-1H-benz[g]indazol-1-yl]benzenesulfonamide;

4-[6-chloro-3-(difluoromethyl)-7-methylthio-1H-benz[g]
indazol-1-yl]benzenesulfonamide;

4-[3-(difluoromethyl)-7-methylsulfinyl-1H-benz[g]indazol-
1-yl]benzenesulfonamide;

4-[6-chloro-3-(difluoromethyl)-7-methylsulfinyl-1H-benz
[g]indazol-1-yl]benzenesulfonamide;

[1-(4-aminosulfonylphenyl)-3-(trifluoromethyl)-1H-benz
[g]indazol-7-yl]carboxylic acid;

methyl [1-(4-aminosulfonylphenyl)-3-(trifluoromethyl)-1H-
benz[g]indazol-7-yl]carboxylate;

[1-(4-aminosulfonylphenyl)-3-(trifluoromethyl)-1H-benz
[g]indazol-7-yl]carbonitrile;

4-[7-hydroxy-3-(trifluoromethyl)-1H-benz[g]indazol-1-yl]
benzenesulfonamide;

4-[7-hydroxymethyl-3-(trifluoromethyl)-1H-benz[g]
indazol-1-yl]benzenesulfonamide;

4-[7-trifluoromethoxy-3-(trifluoromethyl)-1H-benz[g]
indazol-1-yl]benzenesulfonamide;

4-[7-chloro-3-(trifluoromethyl)-1H-benz[g]indazol-1-yl]
benzenesulfonamide;

4-[7-fluoro-3-(trifluoromethyl)-1H-benz[g]indazol-1-yl]
benzenesulfonamide;

4-[7-bromo-3-(trifluoromethyl)-1H-benz[g]indazol-1-yl]
benzenesulfonamide;

4-[7-methyl-3-(trifluoromethyl)-1H-benz[g]indazol-1-yl]
benzenesulfonamide;

4-[7-methoxy-3-(trifluoromethyl)-1H-benz[g]indazol-1-yl]
benzenesulfonamide;

4-[6,7-methylenedioxy-3-(trifluoromethyl)-1H-benz[g]
indazol-1-yl]benzenesulfonamide;

4- [7-dimethylamino-3-(trifluoromethyl)-1H-benz[g]
indazol-1-yl]benzenesulfonamide;

4-[6-fluoro-7-methoxy-3-(trifluoromethyl)-1H-benz[g]
indazol-1-yl]benzenesulfonamide;

4-[6-chloro-7-fluoro-3-(trifluoromethyl)-1H-benz[g]
indazol-1-yl]benzenesulfonamide;

4-[6-chloro-7-methyl-3-(trifluoromethyl)-1H-benz[g]
indazol-1-yl]benzenesulfonamide;

4-[6-fluoro-7-methyl-3-(trifluoromethyl)-1H-benz[g]
indazol-1-yl]benzenesulfonamide;

4-[6,7-dichloro-3-(trifluoromethyl)-1H-benz[g]indazol-1-
yl]benzenesulfonamide;

4-[6,7-difluoro-3-(trifluoromethyl)-1H-benz[g]indazol-1-
yl]benzenesulfonamide;

4-[7-methylthio-3-(trifluoromethyl)-1H-benz[g]indazol-1-
yl]benzenesulfonamide;

4-[6-chloro-7-methylthio-3-(trifluoromethyl)-1H-benz[g]
indazol-1-yl]benzenesulfonamide;

4-[7-methylsulfinyl-3-(trifluoromethyl)-1H-benz[g]indazol-
1-yl]benzenesulfonamide;

4-[6-chloro-7-methylsulfinyl-3-(trifluoromethyl)-1H-benz
[g]indazol-1-yl]benzenesulfonamide; and 4-[6-chloro-7-methoxy-3-(trifluoromethyl)-1H-benz[g]
indazol-1-yl]benzenesulfonamide.

Within Formula I there is a subclass of compounds of high interest represented by Formula II:

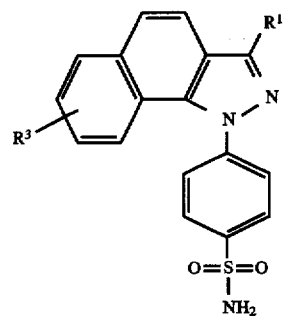

(II)

wherein $R^1$ is hydrido or haloalkyl; and wherein $R^3$ is one or more radicals selected from alkoxy and halo;

or a pharmaceutically-acceptable salt thereof.

A preferred class of compounds consists of those compounds of Formula II wherein $R^1$ is hydrido or lower haloalkyl; and wherein $R^3$ is one or more radicals selected from lower alkoxy and halo; or a pharmaceutically-acceptable salt thereof.

A class of compounds of particular interest consists of those compounds of Formula II wherein $R^1$ is selected from hydrido, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl; and wherein $R^3$ is one or more radicals selected from fluoro, chloro, bromo, methoxy, methylenedioxy, ethoxy, propoxy, n-butoxy and tert-butoxy; or a pharmaceutically-acceptable salt thereof.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" also embraces alkyl radicals having two or more alkoxy radicals attached to the alkyl radical, that is, to form monoalkoxyalkyl and dialkoxyalkyl radicals. More preferred alkoxyalkyl radicals are "lower alkoxyalkyl" radicals having one to six carbon atoms and one or two alkoxy radicals. Examples of such radicals include methoxymethyl, methoxyethyl, ethoxyethyl, methoxybutyl and methoxypropyl. The "alkoxy" or "alkoxyalkyl" radicals may be further substituted with one or more halo atoms, such as fluoro, chloro or bromo, to provide "haloalkoxy" or haloalkoxyalkyl radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. The term "heterocyclic" embraces saturated, partially saturated and unsaturated heteroatom-containing ring-shaped radicals, where the heteroatoms may be selected from nitrogen, sulfur and oxygen. Preferred heterocyclic radicals contain 3 to 10 members. Examples of saturated heterocyclic radicals include saturated 3 to 6-membered heteromonocylic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, dihydrofuran and dihydrothiazole. The term "heteroaryl" embraces unsaturated heterocyclic radicals. Examples of unsaturated heterocyclic radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl, etc.], etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] and isothiazolyl; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuryl, benzothienyl, and the like. Said "heterocyclic" radicals may have 1 to 3 substituents such as lower alkyl, hydroxy, oxo, amino and lower alkylamino. More preferred heteroaryl radicals include five to six membered heteroaryl radicals. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkyl" embraces alkylthio radicals attached to an alkyl radical. More preferred alkylthioalkyl radicals are "lower alkylthioalkyl" radicals having alkyl radicals of one to six carbon atoms and an alkylthio radical as described above. Examples of such radicals include methylthiomethyl. The term "arylthio" embraces radicals containing an aryl radical, attached to a divalent sulfur atom, such as a phenylthio radical. The term "alkylsulfinyl" embraces radicals containing a linear or branched alkyl radical, of one to ten carbon atoms, attached to a divalent —S(=O)— radical. More preferred alkylsulfinyl radicals are "lower alkylsulfinyl" radicals having one to six carbon atoms. Examples of such lower alkylsulfinyl radicals include methylsulfinyl, ethylsulfinyl, butylsulfinyl and hexylsulfinyl. The term "alkylsulfinylalkyl" embraces alkylsulfinyl radicals attached to an alkyl radical, where alkyl and alkylsulfinyl are defined as above. More preferred alkylsulfinylalkyl radicals are "lower alkylsulfinylalkyl" radicals having one to six carbon atoms. Examples of such lower alkylsulfinylalkyl radicals include methylsulfinylmethyl. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The term "alkylsulfonylalkyl" embraces alkylsulfonyl radicals attached to an alkyl radical, where alkyl and alkylsulfonyl are defined as above. More preferred alkylsulfonylalkyl radicals are "lower alkylsulfonylalkyl" radicals having one to six carbon atoms. Examples of such lower alkylsulfonylalkyl radicals include methylsulfonylmethyl, ethylsulfonylmethyl and propylsulfonylmethyl. The term "arylsulfonyl" embraces aryl radicals as defined above, attached to a sulfonyl radical. Examples of such radicals include phenylsulfonyl. The terms "sulfamyl", "aminosulfonyl" and "sulfonamidyl" whether alone or used with terms such as "N-alkylsulfamyl", "N-arylsulfamyl", "N,N-dialkylsulfamyl" and "N-alkyl-N-arylsulfamyl", denote a sulfonyl radical substituted with an amine radical, forming a sulfonamide (—SO$_2$NH$_2$). The terms "N-alkylsulfamyl" and "N,N-dialkylsulfamyl" denote sulfamyl radicals substituted, respectively, with one alkyl radical, a cycloalkyl ring, or two alkyl radicals. The terms "N-arylsulfamyl" and "N-alkyl-N-arylsulfamyl" denote sulfamyl radicals substituted with one aryl radical or one alkyl and one aryl radical, respectively. The term "acyl" denotes a radical provided by the residue after removal of hydroxyl from an organic acid. Examples of such acyl radicals include formyl, alkanoyl and aroyl radicals. The terms "carboxy" or "carboxyl", whether used alone or with other terms, such as "carboxyalkyl", denotes —$CO_2H$. The term "carbonyl", whether used alone or with other terms, such as "alkoxycarbonyl", denotes —(C=O)—. The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "lower alkoxycarbonyl" ester radicals include substituted or unsubstituted methoxycarbonyl, ethoxycarbonyl, propoxycarbonyl, butoxycarbonyl and hexyloxycarbonyl. The term "alkylcarbonyl" includes radicals having alkyl radicals attached to a carbonyl radical. More preferred alkylcarbonyl radicals are "lower alkylcarbonyl" radicals having one to six carbon atoms. Examples of such radicals include methylcarbonyl and ethylcarbonyl. The term "alkylcarbonylalkyl" denotes radicals having alkylcarbonyl attached to alkyl radicals as defined above. More preferred alkylcarbonylalkyl radicals are "lower alkylcarbonylalkyl" radicals having alkyl radicals of one to six carbon atoms. Examples of such radicals include methylcarbonylmethyl and ethylcarbonylmethyl. The term "alkoxycarbonylalkyl" embraces radicals having "alkoxycarbonyl", as defined above substituted to an alkyl radical. More preferred alkoxycarbonylalkyl radicals are "lower alkoxycarbonylalkyl" having lower alkoxycarbonyl radicals as defined above attached to one to six carbon atoms. Examples of such lower alkoxycarbonylalkyl radicals include methoxycarbonylmethyl. The terms "alkanoyl" or "carboxyalkyl" embrace radicals having a carboxy radical as defined above, attached to an alkyl radical. The alkanoyl radicals may be substituted or unsubstituted, such as formyl, acetyl, propionyl, butyryl, isobutyryl, valeryl, isovaleryl, pivaloyl, hexanoyl, trifluoroacetyl or the like, in which the preferable one is formyl, acetyl, propionyl or trifluoroacetyl. The term "aminoalkyl" embraces alkyl radicals substituted with amino radicals. More preferred aminoalkyl radicals are "lower aminoalkyl" having one to six carbon atoms. Examples include aminomethyl, aminoethyl and aminobutyl. The term "alkylaminoalkyl" embraces aminoalkyl radicals having the nitrogen atom substituted with at least one alkyl radical. More preferred alkylaminoalkyl radicals are "lower alkylaminoalkyl" having one to six carbon atoms attached to a lower aminoalkyl radical as described above. The term "alkylamino" denotes amino groups which have been substituted with one or two alkyl radicals. More preferred alkylamino radicals are "lower alkylamino" radicals having one or two alkyl radicals of one to six carbon atoms, attached to a nitrogen atom. Suitable "alkylamino" may be mono or dialkylamino such as N-methylamino, N-ethylamino, N,N-dimethylamino, N,N-diethylamino or the like. The term "alkylaminocarbonyl" embraces alkylamino radicals, as described above, to a carbonyl radical. More preferred alkylaminocarbonyl radicals are "lower alkylaminocarbonyl" having lower alkylamino radicals, as described above, attached to a carbonyl radical. Examples of such radicals include N-methylaminocarbonyl and N,N-dimethylcarbonyl. The terms "N-monoarylaminocarbonyl" and "N-alkyl-N-arylaminocarbonyl" denote aminocarbonyl radicals substituted, respectively, with one aryl radical, and one alkyl and one aryl radical. The term "arylamino" denotes amino groups which have been substituted with one or two aryl radicals, such as N-phenylamino. The "arylamino" radicals may be further substituted on the aryl ring portion of the radical. The term "aminocarbonyl" denotes an amide group of the formula —C(=O)$NH_2$. The term "aminocarbonylalkyl" denotes an aminocarbonyl radical attached to an alkyl radical, as defined above. groupThe term "amidino" denotes an —C(=NH)—$NH_2$ radical. The term "cyanoamidino" denotes an —C(=N—CN)—$NH_2$ radical. The term "cycloalkyl" embraces radicals having three to ten carbon atoms, such as cyclopropyl cyclobutyl, cyclopentyl, cyclohexyl and cycloheptyl. The term "acyl", whether used alone, or within a term such as "acylamino", denotes a radical provided by the residue after removal of hydroxyl from an organic acid. The term "acylamino" embraces an amino radical substituted with an acyl group. An examples of an "acylamino" radical is acetylamino ($CH_3$C(=O)—NH—).

The present invention comprises a pharmaceutical composition comprising a therapeutically-effective amount of a compound of Formula I in association with at least one pharmaceutically-acceptable carrier, adjuvant or diluent.

The present invention also comprises a method of treating inflammation or inflammation-associated disorders in a subject, the method comprising administering to the subject having such inflammation or disorder a therapeutically-effective amount of a compound of Formula I.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The compounds of the invention can be synthesized according to the following procedures of Schemes I–VI, wherein the $R^1$–$R^3$ substituents are as defined for Formula I–II, above, except where further noted.

Scheme I

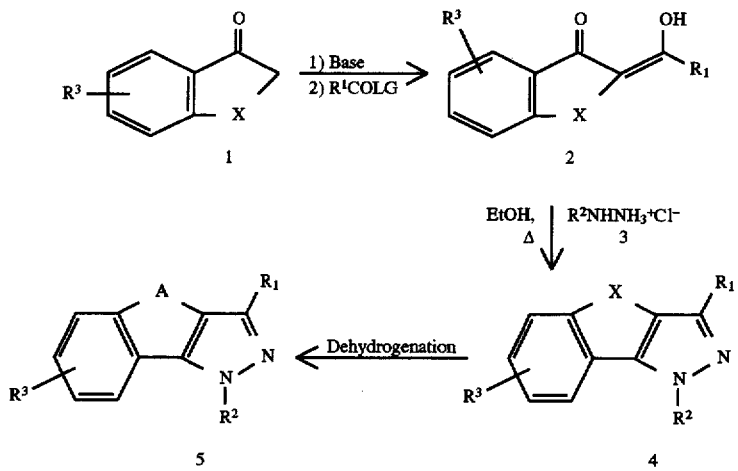

Synthetic Scheme I shows the three step procedure for preparation of fused pyrazole compounds embraced by Formula I. In step 1, a ketone 1 (where X is $(CH_2)_{2-4}$) is reacted with base, such as a lithium base, for example lithium diisopropyl amide (LDA) or LiHMDS, or sodium methoxide (25%) in a protic solvent, such as methanol, followed by condensation with suitable acylating agents $R^1COLG$ (where LG represents an appropriate leaving group such as methoxy, ethoxy, chloro, imidazole, tosyl and the like), such as ethyl trifluoroacetate, in an appropriate solvent such as diethyl ether, methanol or tetrahydrofuran, to give the intermediate diketone 2 (in the enol form). In step 2, the diketone 2 in an anhydrous protic solvent, such as absolute ethanol or acetic acid, is treated with the free base or hydrochloride salt of a phenylhydrazine 3 at reflux for about 24 hours to afford the fused pyrazole 4. In step 3, the fused pyrazole 4 is treated with a dehydrogenating agent such as 2,3-dichloro-5,6-dicyano-1,4-benzoquinone (DDQ). Additional agent can be periodically added to give the partially unsaturated antiinflammatory compounds 5 of this invention. Dehydrogenation simultaneous with halogenation can be achieved by reacting the dihydro fused pyrazole 4 with N-chlorosuccinimide (NCS) and heating to about 50° C. for several days.

Scheme II

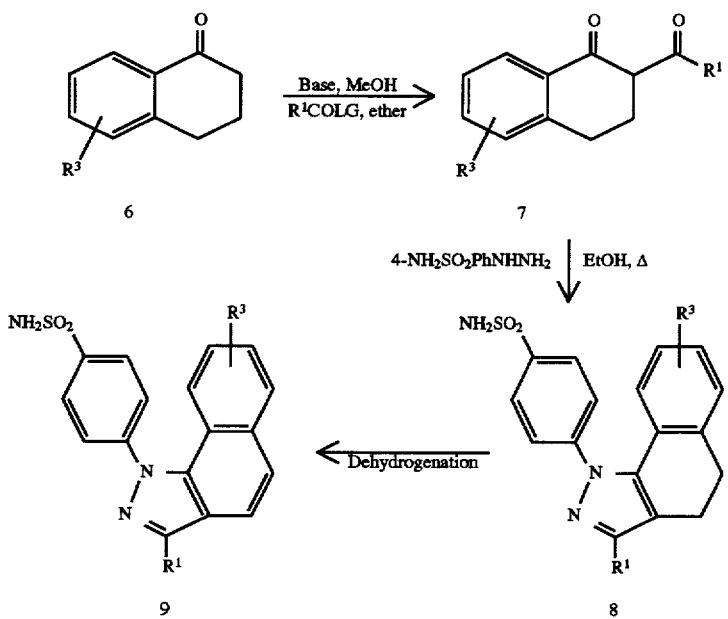

Synthetic Scheme II shows the three step procedure for preparation of benz[g]indazole compounds 9 embraced by Formula I. In step 1, 1-tetralone derivatives 6 are reacted with base, such as lithium diisopropyl amide (LDA) or sodium methoxide (25%) in a protic solvent, such as methanol, followed by condensation with suitable acylating agents $R^1COLG$ (where LG is defined for Scheme I) such as ethyl trifluoroacetate in an appropriate solvent such as diethyl ether, methanol or tetrahydrofuran to give the intermediate diketones 7. In step 2, the diketones 7 in an anhydrous protic solvent, such as absolute ethanol or acetic acid, are treated with the free base or hydrochloride salt of a phenylhydrazine at reflux for 24 hours to afford the 4,5-dihydro-benz[g]indazoles 8. In step 3, the 4,5-dihydro-benz[g]indazoles 8 are reacted with DDQ or N-chlorosuccinimide (NCS) and heated to an appropriate temperature. Additional reagent can be periodically added to give the antiinflammatory compounds 9 of this invention.

SCHEME III

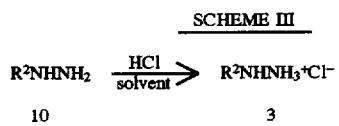

Synthetic Scheme III illustrates a procedure used to prepare the substituted phenylhydrazine hydrochlorides 3 as used in Schemes I–II. The substituted phenylhydrazine is converted to the hydrochloride salt by stirring with a 4N solution of hydrochloric acid in a solvent such as dioxane.

SCHEME IV

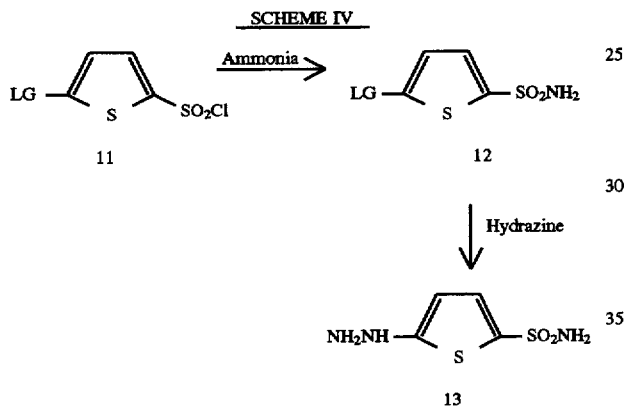

Synthetic Scheme IV shows the two step procedure for preparation of substituted heteroarylhydrazine compounds 13 as used in Scheme I where $R^2$ is thienyl. In step 1, the heteroarylthionyl chloride 11 (where LG represents a leaving group such as halo) is treated with ammonia to give the heteroaryl sulfonamides 12. In step 2, the heteroaryl sulfonamides 12 are treated with hydrazine to give the substituted heteroarylhydrazines 13.

SCHEME V

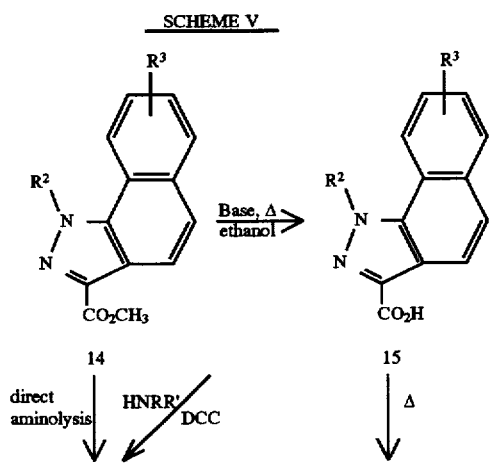

-continued
SCHEME V

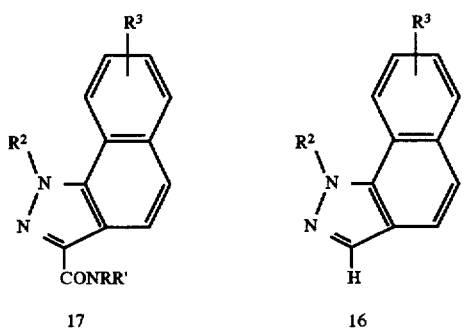

Synthetic Scheme V shows procedures for preparing antiinflammatory agents 15, 16 and 17 of Formula I. The esters 14, which can be prepared as shown in Scheme I, are dissolved in aqueous ethanol and a base such as 10% NaOH is added. The reaction is heated to reflux to give the acids 15. The acids 15 can be decarboxylated to the fused pyrazole 16 by heating to about 290° C. The acids 15 can be converted to the appropriate amides 17 by dissolving in methanol and treating with an appropriate amine in the presence of a coupling agent such as dicyclohexylcarbodiimide (DCC). The amides 17 can also be prepared directly from esters 14 by treating with an appropriate amine.

SCHEME VI

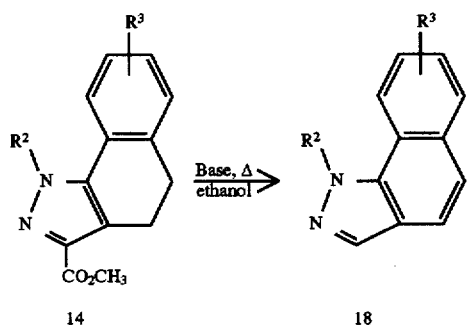

Synthetic Scheme VI shows procedures for preparing antiinflammatory agents 18 of Formula I. The dihydrobenzindazole esters 14, which can be prepared similar to that shown in Scheme I and as shown in Hamilton, *J.Hetyerocyclic Chem.*, 13, 545 (1976), are dissolved in ethanol and a base such as 10% NaOH is added. The reaction is heated to reflux to give the decarboxylated agents 18.

The following examples contain detailed descriptions of the methods of preparation of compounds of Formula I–II. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

EXAMPLE 1

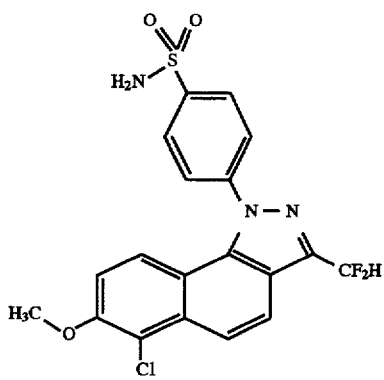

4-[6-Chloro-3-(difluoromethyl)-7-methoxy-1H-benz[g]indazol-1-yl]benzenesulfonamide Step 1 Preparation of 2-[2,2-difluoro-1-hydroxyethylidene]-3,4-dihydro-6-methoxy-1(2H)-naphthalenone A 500 mL one neck round bottomed flask equipped with a nitrogen inlet and provisions for magnetic stirring was charged with ethyl difluoroacetate (6.2 g, 50 mmol) and 75 mL of ether. To this solution was added 12 mL of 25% sodium methoxide in methanol (52.5 mmol). A solution of 6-methoxy-1-tetralone (8.81 g, 50 mmol) in 125 mL of ether was added over about 1 minute. The reaction mixture was stirred at room temperature for 14 hours and was diluted with 150 mL of 1N HCl. The phases were separated and the organic layer was washed with brine, dried over anhydrous $MgSO_4$, filtered and concentrated in vacuo. The residue was taken up in 70 mL of boiling ethanol/water and cooled to room temperature, whereupon crystals of 2-[2,2-difluoro-1-hydroxyethylidene]-3,4-dihydro-6-methoxy-1(2H)-naphthalenone (also known as 6-methoxy-2-difluoroacetyl-1-tetralone) formed which were isolated by filtration and air dried (10.8 g, 85%): mp 52°–54° C.

Step 2 Preparation of 4-[3-(difluoromethyl)-4,5-dihydro-7-methoxy-1H-benz[g]indazol-1-yl]benzenesulfonamide A 500 mL one neck round bottomed flask equipped with reflux condenser, nitrogen inlet and provisions for magnetic stirring was charged with 3,4-dihydro-6-methoxy-2-[2,2-difluoro-1-hydroxyethylidene]-1(2H)-naphthalenone from Step 1 (2.54 g, 10 mmol), 4-sulfonamidophenylhydrazine hydrochloride (2.91 g, 13 mmol) and 250 mL of absolute ethanol. The solution was warmed to reflux for 15 hours and concentrated in vacuo. The residue was dissolved in ethyl acetate, washed with water and with brine, dried over anhydrous $MgSO_4$, filtered and reconcentrated in vacuo. The residue was recrystallized from a mixture of ethanol and water to give 4-[3-(difluoromethyl)-4,5-dihydro-7-methoxy-1H-benz[g]indazol-1-yl]benzenesulfonamide (3.3 g, 82%): mp 256°–257° C.

Step 3 Preparation of 4-[6-Chloro-3-(difluoromethyl)-7-methoxy-1H-benz[g]indazol-1-yl]benzenesulfonamide 4-[3-(Difluoromethyl)-4,5-dihydro-7-methoxy-1H-benz[g]indazol-1-yl]benzenesulfonamide (1.0 g, 1.23 mmol) from Step 2 was suspended in chloroform (100 ml), and N-chlorosuccinimide (NCS) (329 mg, 1.23 mmol) was added. The reaction was heated to 50° C. for 16 hours. At this point, ethanol (20 ml) was added to dissolve the suspended reagents. The reaction was again heated to 50° C. for 24 hours. At this time, an additional equivalent of NCS (329 mg) was added, and the reaction was heated to 50° C. for an additional 4 days. Upon cooling, a precipitate which had formed was collected. This solid was pure 4-[6-chloro-3-(difluoromethyl)-7-methoxy-1H-benz[g]indazol-1-yl] benzenesulfonamide (350 mg, 65%): $^1$H NMR (acetone $d_6$) δ=4.0 (s, 3H), 7.2 (t, 1H, j=54.0 Hz), 7.3 (d, 1H j=9.3 Hz), 7.6 (d, 1H j=9.3 Hz), 7.9 (d, 2H j=8.7 Hz), 8.0 (d, 1H j=9.3 Hz), 8.1 (d, 1H j=9.3 Hz), 8.2 (d, 2H j=8.7 Hz); $^{19}$F NMR (acetone $d_6$) δ–113.5 ppm (d, 2F).

EXAMPLE 2

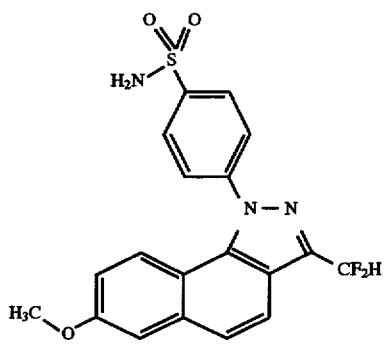

4-[3-(Difluoromethyl)-7-methoxy-1H-benz[g]indazol-1-yl]benzenesulfonamide

4-[3-(Difluoromethyl)-4,5-dihydro-7-methoxy-1H-benz[g]indazol-1-yl]benzenesulfonamide (Example 1, Step 2) (600 mg, 1.5 mmol) was dissolved in 1,4-dioxane (200 ml), and 2,3-dichloro-5,6-dicyano-1,4-benzoquinone (DDQ) (341 mg, 1.5 mmol) was added. The reaction was heated to reflux for 16 hours, at which time a second equivalent of DDQ (340 mg, 1.5 mmol) was added and the reaction was heated to reflux for an additional 24 hours. At three successive 24 hour intervals, 1.5 mmol additional DDQ was added and heating continued until no starting material was left (as determined by thin layer chromatography). The reaction was cooled to room temperature, at which time most of the hydroquinone by-product precipitated. The reaction was filtered and concentrated. The residue was chromatographed on silica gel eluting with 50% ethyl acetate in hexane to yield 4-[3-(difluoromethyl)-7-methoxy-1H-benz[g]indazol-1-yl]benzenesulfonamide (514 mg, 85%): $^1$H NMR (acetone $d_6$) δ=3.9 (s, 3H), 7.05 (m, 1H), 7.2 (t, 1H j=54.0 Hz), 7.5 (m, 2H), 7.7 (m, 1H), 7.9 (m, 3H), 8.2 (d, 2H, j=8.7 Hz); $^{19}$F NMR (acetone $d_6$) δ–113.3 ppm (d, 2F).

EXAMPLE 3

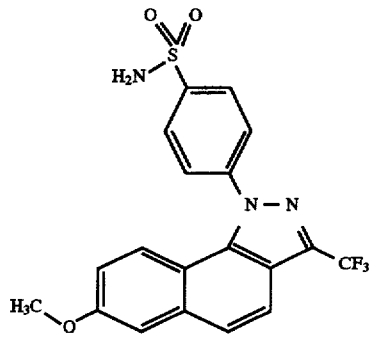

4-[7-Methoxy-3-(trifluoromethyl)-1H-benz[g]indazol-1-yl]benzenesulfonamide

Step 1 Preparation of 3,4-dihydro-6-methoxy-2-[2,2,2-trifluoro-1-hydroxyethylidene]-1(2H)-naphthalenone 6-Methoxytetralone (16.06 g, 91 mmol) was dissolved in ether (150 mL) and tetrahydrofuran (THF) (25 mL), and treated with ethyl trifluoroacetate (14.69 g, 103 mmol) and a sodium methoxide solution (25% in methanol, 24.44 g, 113 mmol). The reaction was stirred for 67.2 hours at room temperature, then treated with 3N HCl (40 mL). The organic layer was collected, washed with brine, dried over $MgSO_4$, and concentrated in vacuo to give a brown solid which was recrystallized from ethanol/water to give the diketone as orange needles (19.67 g, 79%): mp 77°–79° C.; $^1$H NMR ($CDCl_3$) 300 MHz 16.01 (br s, 1H) 7.93 (d, J=8.9 Hz, 1H) 6.87 (dd, J=8.7 Hz J=2.6 Hz, 1H) 6.73 (d, J=2.4 Hz, 1H) 3.87 (s, 3H) 2.86 (m, 2H) 2.74 (m, 2H); $^{19}$F NMR ($CDCl_3$) 300 MHz −71.38 (s). Mass Spectrum $M^+$=273.0688.

Step 2 Preparation of 4-[4,5-dihydro-7-methoxy-3-(trifluoromethyl)-1H-benz[g]indazol-1-yl]benzenesulfonamide 4-Sulfonamidophenylhydrazine hydrochloride (4.35 g, 19.4 mmol) was added to a stirred solution of 3,4-dihydro-6-methoxy-2-[2,2,2-trifluoro-1-hydroxyethylidene]-1(2H)-naphthalenone from Step 1 (5.06 g, 18.6 mmol) in ethanol (100 mL). The reaction was heated to reflux and stirred for 16 hours. The reaction mixture was filtered and washed with ethanol to give the desired pyrazole as a white solid (6.97 g, 88%): mp 277°–278° C.; $^1$H NMR (acetone $d_6$) 300 MHz 8.09 (d, J=8.7 Hz, 2H) 7.80 (d, J=8.9 Hz, 2H) 7.00 (d, J=2.6 Hz, 1H) 6.78 (m, 3H) 6.69 (dd, J=8.7 Hz J=2.6 Hz, 1H) 3.81 (s, 3H) 3.04 (m, 2H) 2.84 (m, 2H); $^{19}$F NMR (acetone $d_6$) 300 MHz −62.43 (s). Mass Spectrum $M^+$=423.0838.

Step 3 Preparation of 4-[7-methoxy-3-(trifluoromethyl)-1H-benz[g]indazol-1-yl]benzenesulfonamide 4-[4,5-Dihydro-7-methoxy-3-(trifluoromethyl)-1H-benz[g]indazol-1-yl]benzenesulfonamide from Step 2 (1.27 g, 3.0 mmol) was dissolved in 1,4-dioxane (200 ml), and DDQ (681 mg, 3.0 mmol) was added. The reaction was heated to reflux for 16 hours at which time a second equivalent of DDQ (681 mg, 3.0 mmol) was added and the reaction was heated to reflux for an additional 24 hours. At three successive 24 hour intervals, 3.0 mmol additional DDQ was added and heating continued until no starting material was left (as determined by thin layer chromatography). The reaction was cooled to room temperature at which time most of the hydroquinone by-product precipitated. The reaction was filtered and concentrated. The residue was chromatographed on silica gel eluting with 50% ethyl acetate in hexane to yield 4-[7-methoxy-3-(trifluoromethyl)-1H-benz[g]indazol-1-yl]benzenesulfonamide (1.1 g, 87%): $^1$H NMR (acetone $d_6$) δ=3.9 (s, 3H), 6.9 (broad s, 2H) 7.1 (m, 1H), 7.6 (m, 2H), 7.8 (m, 2H), 8.0 (d, 2H j=8.7 Hz), 8.2 (d, 2H j=8.7 Hz); $^{19}$F NMR (acetone $d_6$) δ−61.8 ppm (s, 3F).

EXAMPLE 4

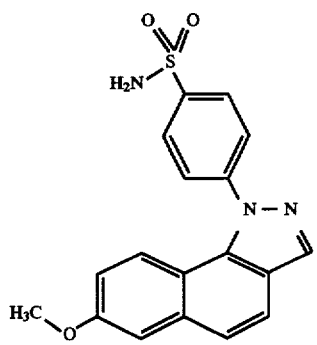

4-[7-Methoxy-1H-benz[g]indazol-1-yl]benzenesulfonamide

Step 1. Preparation of 2-carbomethoxy-6-methoxy-1-tetralone.

A solution of 6-methoxy-1-tetralone (10.0 g, 0.057 mol) and dimethyl oxalate (7.37 g, 0.062 mol) in 100 mL of methanol was treated with a solution of 25% sodium methoxide in methanol. The solution was stirred at room temperature for 16 hours. The dark mixture was treated with 60 mL of 6N hydrochloric acid, whereupon a precipitate formed that was isolated by filtration and air dried to provide 8.65 g (58%) of 2-carbomethoxy-6-methoxy-1-tetralone that was judged to be of sufficient purity to take onto the next step without further purification: $^1$H NMR ($CDCl_3$/300 MHz) 7.99 (1H, d, J=8.66 Hz), 6.87 (1H, dd, J=8.66, 2.42 Hz), 6.72 (1H, d, J=2.42 Hz), 3.91 (3H, s), 3.88 (3H, s), 2.97 (2H, m), 2.86(2H, m).

Step 2. Preparation of 4,5-dihydro-7-methoxy-4-[3-(carbamethoxy)-1H-benz[g]indazol-1-yl]benzenesulfonamide.

A solution of 2-carbomethoxy-6-methoxy-1-tetralone from Step 1 (6.00 g, 22.9 mmol) in 30 mL of anhydrous methanol was warmed to reflux and treated with 4-sulfonamidophenylhydrazine hydrochloride (5.63 g, 25.2 mmol). The solution was maintained at reflux for 14 hours and cooled to room temperature, whereupon the desired pyrazole separated from solution, was isolated by filtration and air dried to afford 8.29 g (88%) of 4,5-dihydro-4-[3-(carbomethoxy)-1H-benz[g]indazol-1-yl]benzenesulfonamide: $^1$H NMR ($CDCl_3$/300 MHz) 7.96 (2H, d, J=8.66 Hz), 7.59 (2H, d, J=8.66 Hz), 6.78 (1H, d, J=2.62 Hz), 6.71 (1H, d, J=8.66 Hz), 6.49 (1H, dd, J=8.66, 2.62 Hz), 6.43 (2H, s), 3.86 (3H, s), 3.70 (3H, s), 2.97–2.97 (4H, m). Mass spectrum M+H=414. Elemental analysis Calc'd. for $C_{20}H_{19}N_3O_5S$: C, 58.1; H, 4.63; N, 10.16; S, 7.75. Found: C, 58.20; H, 4.59; N, 10.19; S, 7.69.

Step 3. Preparation of 4,5-dihydro-7-methoxy-4-[3-(carboxy)-1H-benz[g]indazol-1-yl]benzenesulfonamide.

A solution of 4,5-dihydro-4-[3-(carbomethoxy)-1H-benz[g]indazol-1-yl]benzenesulfonamide from Step 2 (3.00 g, 7.26 mmol) in 25 mL of dioxane was treated with 2.5N sodium hydroxide (7.3 mL, 18.1 mmol) and 5 mL of water. The solution was warmed to reflux and after 1 hour the solution was cooled to room temperature and acidified by the addition of excess 6N hydrochloric acid. The acid separated as a white solid and was isolated by filtration and air dried to provide 2.41 g (83%) of pure acid that was used directly in the next step: $^1$H NMR ($CD_3OD$): 8.09 (2H, d, J=8.66 Hz), 7.74 (2H, d, J=8.66 Hz), 6.96 (1H, d, J=2.62 Hz), 6.70 (1H, d, J=8.66 Hz), 6.60 (1H, dd, J=8.66, 2.62 Hz), 3.78 (3H, s), 3.01(4H, s). Mass spectrum M+H=400.

Step 4. Preparation of 4-[7-methoxy-1H-benz[g]indazol-1-yl]benzenesulfonamide.

4,5-Dihydro-4- [3-(carboxy)-1H-benz[g]indazol-1-yl]benzenesulfonamide from Step 3 (1.00 g, 2.5 mmol) was placed in a round bottomed flask and heated to 295° C. for 0.5 hour. The residue was dissolved in a small amount of ethyl acetate and purified by flash chromatography, eluting with 40% ethyl acetate in hexane to give 4-[7-methoxy-1H-benz[g]indazol-1-yl]benzenesulfonamide as a white solid (200 mg, 20%): $^1$H NMR ($CD_3OD$): 8.28 (1H, s), 8.18 (2H, d, J=8.66 Hz), 7.81 (1H, s), 7.77 (2H, d, J=8.66 Hz), 7.59 (1H, d, J=8.86 Hz), 7.52 (1H, d, J=9.27 Hz), 7.46 (1H, d, J=2.62 Hz), 7.0 (1H, dd, J=9.27, 2.62 Hz), 3.91 (3H, s) . Mass spectrum M+H =354. Elemental analysis Calc'd. for $C_{18}H_{15}N_3O_3S$: C, 61.18; H, 4.28; N, 11.89; S, 9.07. Found: C, 60.93; H, 4.23; N, 11.73; S, 8.93.

EXAMPLE 5

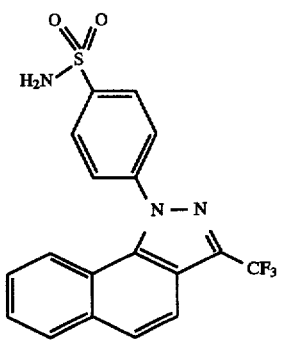

4-[3-(Trifluoromethyl)-1H-benz[g]indazol-1-yl]
benzenesulfonamide

Step 1 Preparation of 3,4-dihydro-2-[2,2,2-trifluoro-1-hydroxyethylidene]-1(2H)-naphthalenone A 250 mL one neck round bottomed flask equipped with a reflux condenser, nitrogen inlet and provisions for magnetic stirring was charged with ethyl trifluoroacetate (28.4 g, 0.2 mol) and 75 mL of ether. To this solution was added 48 mL of 25% sodium methoxide in methanol (0.21 mol). A solution of 1-tetralone (29.2 g, 0.2 mol) in ether (50 mL) was added over about 5 minutes The reaction mixture was stirred at room temperature for 14 hours and was diluted with 100 mL of 3N HCl. The phases were separated, and the organic layer was washed with 3N HCl and with brine, dried over anhydrous MgSO$_4$, filtered and concentrated in vacuo. The residue was taken up in 70 mL of boiling ethanol/water and cooled to room temperature, whereupon crystals of 3,4-dihydro-2-[2,2,2-trifluoro-1-hydroxyethylidene]-1(2H)-naphthalenone formed which were isolated by filtration and air dried to give 32 g (81%) of pure 3,4-dihydro-2-[2,2,2-trifluoro-1-hydroxyethylidene]-1(2H)-naphthalenone: mp 48°–49° C.; $^1$H NMR (CDCl$_3$) δ 2.8 (m, 2H), 2.9 (m, 2H), 7.2 (d, j=3.0 Hz, 1H), 7.36 (m, 1H), 7.50 (m, 1H), 7.98 (m, 1H); $^{19}$F NMR (CDCl$_3$) δ–72.0. EI GC-MS M$^+$=242.

Step 2 Preparation of 4,5-dihydro-4-[3-(trifluoromethyl)-1H-benz[g]indazol-1-yl]benzenesulfonamide A 100 mL one neck round bottomed flask equipped with reflux condenser, nitrogen inlet and provisions for magnetic stirring was charged with 3,4-dihydro-2-[2,2,2-trifluoro-1-hydroxyethylidene]-1(2H)-naphthalenone from Step 1 (1.21 g, 5.0 mmol), 4-sulfonamidophenylhydrazine hydrochloride (1.12 g, 5.0 mmol) and 25 mL of absolute ethanol. The solution was warmed to reflux for 15 hours, cooled and concentrated in vacuo. The residue was dissolved in ethyl acetate, washed with water and with brine, dried over anhydrous MgSO$_4$, filtered and reconcentrated in vacuo. The residue was recrystallized from a mixture of ethyl acetate and isooctane to give 1.4 g (71%) of pure 4,5-dihydro-4-[3-(trifluoromethyl)-1H-benz[g]indazol-1-yl]benzenesulfonamide: mp 257°–258° C.; $^1$H NMR (CDCl$_3$/CD$_3$OD, 4:1) δ 2.7 (m, 2H), 2.9 (m, 2H), 6.6 (m, 1H), 6.9 (m, 1H), 7.1 (m, 1H), 7.16 (m, 1H), 7.53 (m, 2H), 7.92 (m, 2H); $^{19}$F NMR CDCl$_3$ δ–62.5. FAB-MS M$^+$H=394.

Step 3 Preparation of 4-[3-(trifluoromethyl)-1H-benz[g]indazol-1-yl]benzenesulfonamide 4,5-Dihydro-4-[3-(trifluoromethyl)-1H-benz[g]indazol-1-yl]benzenesulfonamide from Step 2 (393 mg, 1.0 mmol) was dissolved in 1,4-dioxane (50 ml), and 2,3-dichloro-5,6-dicyano-1,4-benzoquinone (DDQ) (227 mg, 1.0 mmol) was added. The reaction was heated to reflux for 16 hours at which time a second equivalent of DDQ (227 mg, 1.0 mmol) was added and the reaction was heated to reflux for an additional 24 hours. At three successive 24 hour intervals, 1.0 mmol additional DDQ was added and heating continued until no starting material was left. The reaction was cooled to room temperature at which time most of the hydroquinone by-product precipitated. The reaction was filtered and concentrated. The residue was chromatographed on silica gel eluting with 50% ethyl acetate in hexane to yield 4-[3-(trifluoromethyl)-1H-benz[g]indazol-1-yl]benzenesulfonamide (352 mg, 90%): $^1$H NMR (acetone d$_6$) δ=6.89 (broad s, 2H), 7.5 (m, 1H), 7.7 (m, 2H), 7.89 (s, 2H), 8.0 (d, 2H, j=8.7 Hz), 8.15 (d, 1H, j=8.3 Hz), 8.3 (d, 2H, j=8.7 Hz); $^{19}$F NMR (acetone d$_6$) δ–61.7 ppm (s, 3F).

BIOLOGICAL EVALUATION

Rat Carrageenan Foot Pad Edema Test

The carrageenan foot edema test was performed with materials, reagents and procedures essentially as described by Winter, et al., (Proc. Soc. Exp. Biol. Med., 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterhess and Bliven, Laboratory Models for Testing NSAIDs, in Non-steroidal Anti-Inflammatory Drugs, (J. Lombardino, ed. 1985)). The % inhibition shows the % decrease from control paw volume determined in this procedure and the data for selected compounds in this invention are summarized in Table I.

TABLE I

| RAT PAW EDEMA | |
|---|---|
| Example | % Inhibition[1] |
| 1 | 29 |
| 2 | 24 |

[1] @ 30 mg/kg body weight

Evaluation of COX I and COX II activity in vitro

The compounds of this invention exhibited inhibition in vitro of COX II. The COX II inhibition activity of the compounds of this invention illustrated in the Examples was determined by the following methods.

a. Preparation of recombinant CQX baculoviruses

A 2.0 kb fragment containing the coding region of either human or murine COX-I or human or murine COX-II was cloned into a BamH1 site of the baculovirus transfer vector pVL1393 (Invitrogen) to generate the baculovirus transfer vectors for COX-I and COX-II in a manner similar to the method of D. R. O'Reilly et al (Baculovirus Expression Vectors: A Laboratory Manual (1992)). Recombinant baculoviruses were isolated by transfecting 4 μg of baculovirus transfer vector DNA into SF9 insect cells (2×10e8) along with 200 ng of linearized baculovirus plasmid DNA by the calcium phosphate method. See M. D. Summers and G. E. Smith, *A Manual of Methods for Baculovirus Vectors and Insect Cell Culture Procedures*, Texas Agric. Exp. Station Bull. 1555 (1987). Recombinant viruses were purified by three rounds of plaque purification and high titer (10E7–10E8 pfu/ml) stocks of virus were prepared. For large scale production, SF9 insect cells were infected in 10 liter fermentors ($0.5 \times 10^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000×G for 30 minutes, and the resultant supernatant was stored at −80° C. before being assayed for COX activity.

b. Assay for COX I and COX II activity:

COX activity was assayed as $PGE_2$ formed/µg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 µM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 µl of reaction mix into 160 µl ELISA buffer and 25 µM indomethacin. The $PGE_2$ formed was measured by standard ELISA technology (Cayman Chemical). Results are shown in Table II.

TABLE II

| Example | Human COX II ID$_{50}$ µM | Human COX I ID$_{50}$ µM |
|---|---|---|
| 1 | 1 | >100 |
| 2 | <1 | .8 |
| 3 | <1 | >100 |
| 4 | >100 | >100 |
| 5 | >100 | >100 |

Also embraced within this invention is a class of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably between about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I

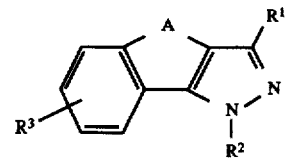

(I)

wherein A is —(CH$_2$)$_m$—CH=CH—(CH$_2$)$_n$—;

wherein m is 0 or 1;

wherein n is 0 or 1;

wherein R$^1$ is selected from hydrido, halo, haloalkyl, cyano, nitro, formyl, alkoxycarbonyl, carboxyl, carboxyalkyl, alkoxycarbonylalkyl, amidino, cyanoamidino, aminocarbonyl, alkoxy, alkoxyalkyl, aminocarbonylalkyl, N-monoalkylaminocarbonyl, N-monoarylaminocarbonyl, N,N-dialkylaminocarbonyl, N-alkyl-N-arylaminocarbonyl, alkylcarbonyl, alkylcarbonylalkyl, hydroxyalkyl, alkylthio, alkylsulfinyl, alkylsulfonyl, alkylthioalkyl, alkylsulfinylalkyl, alkylsulfonylalkyl, N-alkylsulfamyl, N-arylsulfamyl, arylsulfonyl, N,N-dialkylsulfamyl, N-alkyl-N-arylsulfamyl, and heterocyclic;

wherein R$^2$ is selected from aryl and heteroaryl, wherein R$^2$ is optionally substituted at a substitutable position with one or more radicals selected from alkylsulfonyl, sulfamyl, halo, alkyl, alkoxy, hydroxyl, and haloalkyl; and wherein $R^3$ is one or more radicals selected from hydrido, halo, alkyl, alkylthio, alkylsulfinyl, alkylsulfonyl, cyano, carboxyl, alkoxycarbonyl, aminocarbonyl, N-monoalkylaminocarbonyl, N-monoarylaminocarbonyl, N,N-dialkylaminocarbonyl, N-alkyl-N-arylaminocarbonyl, haloalkyl, hydroxyl, alkoxy, hydroxyalkyl, haloalkoxy, sulfamyl, N-alkylsulfamyl, amino, N-alkylamino, N,N-dialkylamino, heterocyclic, nitro, and acylamino;

provided either $R^2$ is substituted with a radical selected from alkylsulfonyl and sulfamyl, or $R^3$ is alkylsulfonyl or sulfamyl;

or a pharmaceutically-acceptable salt thereof.

2. Compound of claim 1 wherein A is —$(CH_2)_m$—CH=CH—$(CH_2)_n$—;
wherein m is 0 or 1;
wherein n is 0 or 1;
wherein $R^1$ is selected from halo, lower haloalkyl, cyano, nitro, formyl, lower alkoxycarbonyl, lower carboxyalkyl, lower alkoxycarbonylalkyl, amidino, cyanoamidino, lower alkoxy, lower alkoxyalkyl, lower aminocarbonylalkyl, lower N-monoalkylaminocarbonyl, N-phenylaminocarbonyl, lower N,N-dialkylaminocarbonyl, lower N-alkyl-N-phenylaminocarbonyl, lower alkylcarbonyl, lower alkylcarbonylalkyl, lower hydroxyalkyl, lower alkylthio, lower alkylsulfinyl, lower alkylsulfonyl, lower alkylthioalkyl, lower alkylsulfinylalkyl, lower alkylsulfonylalkyl, lower N-alkylsulfamyl, N-phenylsulfamyl, phenylsulfonyl, lower N,N-dialkylsulfamyl, lower N-alkyl-N-phenylsulfamyl and five-seven membered heterocyclic;

wherein $R^2$ is selected from phenyl and five or six membered heteroaryl, wherein $R^2$ is optionally substituted at a substitutable position with one or more radicals selected from lower alkylsulfonyl, sulfamyl, hydrido, halo, lower alkyl, lower alkoxy, hydroxyl and lower haloalkyl; and wherein $R^3$ is one or more radicals selected from halo, lower alkylthio, lower alkylsulfinyl, lower alkyl, lower alkylsulfonyl, cyano, carboxyl, lower alkoxycarbonyl, aminocarbonyl, lower N-monoalkylaminocarbonyl, N-phenylaminocarbonyl, lower N,N-dialkylaminocarbonyl, lower N-alkyl-N-phenylaminocarbonyl, lower haloalkyl, hydroxyl, lower alkoxy, lower hydroxyalkyl, lower haloalkoxy, sulfamyl, lower N-alkylsulfamyl, amino, lower N-alkylamino, lower N,N-dialkylamino, five-seven membered heterocyclic, nitro and acylamino;

or a pharmaceutically-acceptable salt thereof.

3. Compound of claim 2 wherein A is —CH=CH—; wherein $R^1$ is selected from halo, lower haloalkyl, cyano, nitro, formyl, lower alkoxycarbonyl, lower carboxyalkyl, lower alkoxy, lower N-monoalkylaminocarbonyl, N-phenylaminocarbonyl, lower N,N-dialkylaminocarbonyl, lower N-alkyl-N-phenylaminocarbonyl, lower alkylcarbonyl and lower hydroxyalkyl; wherein $R^2$ is phenyl substituted at a substitutable position with a radical selected from lower alkylsulfonyl and sulfamyl; and wherein $R^3$ is one or more radicals selected from halo, lower alkylthio, lower alkylsulfinyl, lower alkyl, lower alkylsulfonyl, cyano, carboxyl, lower alkoxycarbonyl, aminocarbonyl, lower N-monoalkylaminocarbonyl, N-phenylaminocarbonyl, lower N,N-dialkylaminocarbonyl, lower N-alkyl-N-phenylaminocarbonyl, lower haloalkyl, hydroxyl, lower alkoxy, lower hydroxyalkyl, lower haloalkoxy, amino, lower N-alkylamino, lower N,N-dialkylamino, nitro and acylamino; or a pharmaceutically-acceptable salt thereof.

4. Compound of claim 3 wherein A is —CH=CH—; wherein $R^1$ is selected from lower haloalkyl, cyano, lower alkoxycarbonyl, lower N-monoalkylaminocarbonyl, N-phenylaminocarbonyl, lower N,N-dialkylaminocarbonyl and lower N-alkyl-N-phenylaminocarbonyl; wherein $R^2$ is phenyl substituted at a substitutable position with a radical selected from lower alkylsulfonyl and sulfamyl; and wherein $R^3$ is one or more radicals selected from halo, lower alkylthio, lower alkylsulfinyl, lower alkyl, cyano, lower alkoxycarbonyl, aminocarbonyl, lower N-monoalkylaminocarbonyl, lower haloalkyl, hydroxyl, lower alkoxy, lower hydroxyalkyl, lower haloalkoxy, amino, lower N,N-dialkylamino and nitro; or a pharmaceutically-acceptable salt thereof.

5. Compoud of claim 4 wherein A is —CH=CH—; wherein $R^1$ is selected from fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, N-methylaminocarbonyl, N-phenylaminocarbonyl, N,N-dimethylaminocarbonyl and N-methyl-N-phenylaminocarbonyl; wherein $R^2$ is phenyl substituted at a substitutable position with methylsulfonyl or sulfamyl; and wherein $R^3$ is one or more radicals selected from fluoro, chloro, bromo, methylthio, ethylthio, isopropylthio, tert-butylthio, isobutylthio, hexylthio, methylsulfinyl, ethylsulfinyl, isopropylsulfinyl, tert-butylsulfinyl, isobutylsulfinyl, hexylsulfinyl, methyl, ethyl, isopropyl, tert-butyl, isobutyl, hexyl, cyano, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, aminocarbonyl, N-methylaminocarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, hydroxymethyl, trifluoromethoxy, amino, N,N-dimethylamino and nitro; or a pharmaceutically-acceptable salt thereof.

6. Compound of claim 5 selected from compounds, and their pharmaceutically acceptable salts, of the group consisting of 4-[6-chloro-7-methoxy-1H-benz[g]indazol-1-yl]benzenesulfonamide;

[1-(4-aminosulfonylphenyl)-6-chloro-7-methoxy-1H-benz[g]indazol-3-yl]carbonitrile;

methyl [1-(4-aminosulfonylphenyl)-6-chloro-7-methoxy-1H-benz[g]indazol-3-yl]carboxylate;

N-methyl [1-(4-aminosulfonylphenyl)-6-chloro-7-methoxy-1H-benz[g]indazol-3-yl]carboxamide;

6-chloro-7-methoxy-1-(4-methylsulfonylphenyl)-1H-benz[g]indazole;

[1-(4-methylsulfonylphenyl)-6-chloro-7-methoxy-1H-benz[g]indazol-3-yl]carbonitrile;

ethyl [1-(4-methylsulfonylphenyl)-6-chloro-7-methoxy-1H-benz[g]indazol-3-yl]carboxylate;

N-methyl [1-(4-methylsulfonylphenyl)-6-chloro-7-methoxy-1H-benz[g]indazol-3-yl]carboxamide;

7-chloro-3-(difluoromethyl)-1-(4-methylsulfonylphenyl)-1H-benz[g]indazole;

3-(difluoromethyl)-7-fluoro-1-(4-methylsulfonylphenyl)-1H-benz[g]indazole;
3-(difluoromethyl)-7-methyl-1-(4-methylsulfonylphenyl)-1H-benz[g]indazole;
3-(difluoromethyl)-7-methoxy-1-(4-methylsulfonylphenyl)-1H-benz[g]indazole;
3-(difluoromethyl)-6,7-methylenedioxy-1-(4-methylsulfonylphenyl)-H-benz[g]indazole;
3-(difluoromethyl)-6-fluoro-7-methoxy-1-(4-methylsulfonylphenyl)-1H-benz[g]indazole;
6-chloro-3-(difluoromethyl)-7-fluoro-1-(4-methylsulfonylphenyl)-1H-benz[g]indazole;
6-chloro-3-(difluoromethyl)-7-methyl-1-(4-methylsulfonylphenyl)-1H-benz[g]indazole;
3-(difluoromethyl)-6-fluoro-7-methyl-1-(4-methylsulfonylphenyl)-1H-benz[g]indazole;
6,7-dichloro-3-(difluoromethyl)-1-(4-methylsulfonylphenyl)-1H-benz[g]indazole;
6,7-difluoro-3-(difluoromethyl)-1-(4-methylsulfonylphenyl)-1H-benz[g]indazole;
[1-(4-methylsulfonylphenyl)-3-(trifluoromethyl)-1H-benz[g]indazol-7-yl]carboxylic acid;
methyl [1-(4-methylsulfonylphenyl)-3-(trifluoromethyl)-1H-benz[g]indazol-7-yl]carboxylate;
7-chloro-1-(4-methylsulfonylphenyl)-3-(trifluoromethyl)-1H-benz[g]indazole;
7-fluoro-1-(4-methylsulfonylphenyl)-3-(trifluoromethyl)-1H-benz[g]indazole;
7-methyl-1-(4-methylsulfonylphenyl)-3-(trifluoromethyl)-1H-benz[g]indazole;
7-methoxy-1-(4-methylsulfonylphenyl)-3-(trifluoromethyl)-1H-benz[g]indazole;
6,7-methylenedioxy-1-(4-methylsulfonylphenyl)-3-(trifluoromethyl)-1H-benz[g]indazole;
6-fluoro-7-methoxy-1-(4-methylsulfonylphenyl)-3-(trifluoromethyl)-1H-benz[g]indazole;
6-chloro-7-fluoro-1-(4-methylsulfonylphenyl)-3-(trifluoromethyl)-1H-benz[g]indazole;
6-chloro-7-methyl-1-(4-methylsulfonylphenyl)-3-(trifluoromethyl)-1H-benz[g]indazole;
6-fluoro-7-methyl-1-(4-methylsulfonylphenyl)-3-(trifluoromethyl)-1H-benz[g]indazole;
6,7-dichloro-1-(4-methylsulfonylphenyl)-3-(trifluoromethyl)-1H-benz[g]indazole;
6,7-difluoro-1-(4-methylsulfonylphenyl)-3-(trifluoromethyl)-1H-benz[g]indazole;
6-chloro-1-(4-methylsulfonylphenyl)-7-methylthio-3-(trifluoromethyl)-1H-benz[g]indazole;
6-chloro-7-methylsulfinyl-1-(4-methylsulfonylphenyl)-3-(trifluoromethyl)-1H-benz[g]indazole;
6-chloro-7-methoxy-1-(4-methylsulfonylphenyl)-3-(trifluoromethyl)-1H-benz[g]indazole;
[1-(4-aminosulfonylphenyl)-3-(difluoromethyl)-1H-benz[g]indazol-7-yl]carboxylic acid;
methyl [1-(4-aminosulfonylphenyl)-3-(difluoromethyl)-1H-benz[g]indazol-7-yl]carboxylate;
[1-(4-aminosulfonylphenyl)-3-(difluoromethyl)-1H-benz[g]indazol-7-yl]carbonitrile;
4-[7-chloro-3-(difluoromethyl)-1H-benz[g]indazol-1-yl]benzenesulfonamide;
4-[3-(difluoromethyl)-7-fluoro-1H-benz[g]indazol-1-yl]benzenesulfonamide;
4-[7-bromo-3-(difluoromethyl)-1H-benz[g]indazol-1-yl]benzenesulfonamide;
4-[3-(difluoromethyl)-7-methyl-1H-benz[g]indazol-1-yl]benzenesulfonamide;
4-[3-(difluoromethyl)-7-methoxy-1H-benz[g]indazol-1-yl]benzenesulfonamide;
4-[3-(difluoromethyl)-6,7-methylenedioxy-1H-benz[g]indazol-1-yl]benzenesulfonamide;
4-[3-(difluoromethyl)-6-fluoro-7-methoxy-1H-benz[g]indazol-1-yl]benzenesulfonamide;
4-[6-chloro-3-(difluoromethyl)-7-fluoro-1H-benz[g]indazol-1-yl]benzenesulfonamide;
4-[6-chloro-3-(difluoromethyl)-7-methyl-1H-benz[g]indazol-1-yl]benzenesulfonamide;
4-[3-(difluoromethyl)-6-fluoro-7-methyl-1H-benz[g]indazol-1-yl]benzenesulfonamide;
4-[6,7-dichloro-3-(difluoromethyl)-1H-benz[g]indazol-1-yl]benzenesulfonamide;
4-[6,7-difluoro-3-(difluoromethyl)-1H-benz[g]indazol-1-yl]benzenesulfonamide;
4-[6-chloro-3-(difluoromethyl)-7-methylthio-1H-benz[g]indazol-1-yl]benzenesulfonamide;
4-[6-chloro-3-(difluoromethyl)-7-methylsulfinyl-1H-benz[g]indazol-1-yl]benzenesulfonamide;
[1-(4-aminosulfonylphenyl)-3-(trifluoromethyl)-1H-benz[g]indazol-7-yl]carboxylic acid;
methyl [1-(4-aminosulfonylphenyl)-3-(trifluoromethyl)-1H-benz[g]indazol-7-yl]carboxylate;
[1-(4-aminosulfonylphenyl)-3-(trifluoromethyl)-1H-benz[g]indazol-7-yl]carbonitrile;
4-[7-chloro-3-(trifluoromethyl)-1H-benz[g]indazol-1-yl]benzenesulfonamide;
4-[7-fluoro-3-(trifluoromethyl)-1H-benz[g]indazol-1-yl]benzenesulfonamide;
4-[7-methyl-3-(trifluoromethyl)-1H-benz[g]indazol-1-yl]benzenesulfonamide;
4-[7-methoxy-3-(trifluoromethyl)-1H-benz[g]indazol-1-yl]benzenesulfonamide;
4-[6,7-methylenedioxy-3-(trifluoromethyl)-1H-benz[g]indazol-1-yl]benzenesulfonamide;
4-[7-dimethylamino-3-(trifluoromethyl)-1H-benz[g]indazol-1-yl]benzenesulfonamide;
4-[6-fluoro-7-methoxy-3-(trifluoromethyl)-1H-benz[g]indazol-1-yl]benzenesulfonamide;
4-[6-chloro-7-fluoro-3-(trifluoromethyl)-1H-benz[g]indazol-1-yl]benzenesulfonamide;
4-[6-chloro-7-methyl-3-(trifluoromethyl)-1H-benz[g]indazol-1-yl]benzenesulfonamide;
4-[6-fluoro-7-methyl-3-(trifluoromethyl)-1H-benz[g]indazol-1-yl]benzenesulfonamide;
4-[6,7-dichloro-3-(trifluoromethyl)-1H-benz[g]indazol-1-yl]benzenesulfonamide;
4-[6,7-difluoro-3-(trifluoromethyl)-1H-benz[g]indazol-1-yl]benzenesulfonamide;
4-[6-chloro-7-methylthio-3-(trifluoromethyl)-1H-benz[g]indazol-1-yl]benzenesulfonamide;
4-[6-chloro-7-methylsulfinyl-3-(trifluoromethyl)-1H-benz[g]indazol-1-yl]benzenesulfonamide; and
4-[6-chloro-7-methoxy-3-(trifluoromethyl)-1H-benz[g]indazol-1-yl]benzenesulfonamide.

7. Compound of claim 5 which is 4-[6-chloro-7-methoxy-3-(trifluoromethyl)-1H-benz[g]indazol-1-yl]benzenesulfonamide, or a pharmaceutically-acceptable salt thereof.

8. Compound of claim 5 which is 4-[3-difluoromethyl)-7-methoxy-1H-benz[g]indazol-1-yl]benzenesulfonamide, or a pharmaceutically-acceptable salt thereof.

9. A compound of Formula II

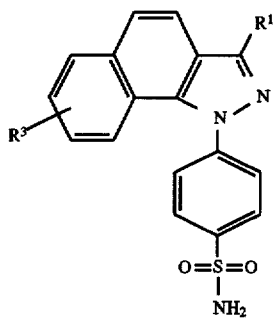
(II)

wherein $R^1$ is hydrido or haloalkyl; and
wherein $R^3$ is one or more radicals selected from alkoxy and halo;
or a pharmaceutically-acceptable salt thereof.

10. Compound of claim 9 wherein $R^1$ is hydrido or lower haloalkyl; and wherein $R^3$ is one or more radicals selected from lower alkoxy and halo; or a pharmaceutically-acceptable salt thereof.

11. Compound of claim 10 wherein $R^1$ is selected from hydrido, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl; and wherein $R^3$ is one or more radicals selected from fluoro, chloro, bromo, methoxy, methylenedioxy, ethoxy, propoxy, n-butoxy and tert-butoxy; or a pharmaceutically-acceptable salt thereof.

12. A pharmaceutical composition comprising a therapeutically-effective amount of a compound, said compound selected from a family of compounds of claim 1; or a pharmaceutically-acceptable salt thereof.

13. A pharmaceutical composition comprising a therapeutically-effective amount of a compound, said compound selected from a family of compounds of claim 2; or a pharmaceutically-acceptable salt thereof.

14. A pharmaceutical composition comprising a therapeutically-effective amount of a compound, said compound selected from a family of compounds of claim 3; or a pharmaceutically-acceptable salt thereof.

15. A pharmaceutical composition comprising a therapeutically-effective amount of a compound, said compound selected from a family of compounds of claim 4; or a pharmaceutically-acceptable salt thereof.

16. A pharmaceutical composition comprising a therapeutically-effective amount of a compound, said compound selected from a family of compounds of claim 5; or a pharmaceutically-acceptable salt thereof.

17. A pharmaceutical composition comprising a therapeutically-effective amount of a compound, said compound selected from a family of compounds of claim 6; or a pharmaceutically-acceptable salt thereof.

18. A pharmaceutical composition comprising a therapeutically-effective amount of a compound, said compound selected from a family of compounds of claim 7; or a pharmaceutically-acceptable salt thereof.

19. A pharmaceutical composition comprising a therapeutically-effective amount of a compound, said compound selected from a family of compounds of claim 8; or a pharmaceutically-acceptable salt thereof.

20. A method of treating inflammation or an inflammation-associated disorder in a subject, said method comprising administering to the subject having or susceptible to said inflammation or inflammation-associated disorder, a therapeutically-effective amount of a compound of claim 1; further provided that $R^3$ is not hydrido when $R^1$ is trifluoromethyl; and further provided that $R^1$ is not hydrido when $R^3$ is a single methoxy radical; or a pharmaceutically-acceptable salt thereof.

21. A method of treating inflammation or an inflammation-associated disorder in a subject, said method comprising administering to the subject having or susceptible to said inflammation or inflammation-associated disorder, a therapeutically-effective amount of a compound of claim 2; or a pharmaceutically-acceptable salt thereof.

22. A method of treating inflammation or an inflammation-associated disorder in a subject, said method comprising administering to the subject having or susceptible to said inflammation or inflammation-associated disorder, a therapeutically-effective amount of a compound of claim 3; or a pharmaceutically-acceptable salt thereof.

23. A method of treating inflammation or an inflammation-associated disorder in a subject, said method comprising administering to the subject having or susceptible to said inflammation or inflammation-associated disorder, a therapeutically-effective amount of a compound of claim 4; or a pharmaceutically-acceptable salt thereof.

24. A method of treating inflammation or an inflammation-associated disorder in a subject, said method comprising administering to the subject having or susceptible to said inflammation or inflammation-associated disorder, a therapeutically-effective amount of a compound of claim 5; or a pharmaceutically-acceptable salt thereof.

25. A method of treating inflammation or an inflammation-associated disorder in a subject, said method comprising administering to the subject having or susceptible to said inflammation or inflammation-associated disorder, a therapeutically-effective amount of a compound of claim 6; or a pharmaceutically-acceptable salt thereof.

26. A method of treating inflammation or an inflammation-associated disorder in a subject, said method comprising administering to the subject having or susceptible to said inflammation or inflammation-associated disorder, a therapeutically-effective amount of a compound of claim 7; or a pharmaceutically-acceptable salt thereof.

27. A method of treating inflammation or an inflammation-associated disorder in a subject, said method comprising administering to the subject having or susceptible to said inflammation or inflammation-associated disorder, a therapeutically-effective amount of a compound of claim 8; or a pharmaceutically-acceptable salt thereof.

28. The method of claim 20 for use in treatment of inflammation.

29. The method of claim 20 for use in treatment of an inflammation-associated disorder.

30. The method of claim 29 wherein the inflammation-associated disorder is arthritis.

31. The method of claim 29 wherein the inflammation-associated disorder is pain.

32. The method of claim 29 wherein the inflammation-associated disorder is fever.

* * * * *